US 6,461,321 B1
Oct. 8, 2002

(12) United States Patent
Quinn

(54) HEMODIALYSIS CATHETER

(75) Inventor: David G. Quinn, Grayslake, IL (US)

(73) Assignee: Radius International Limited Partnership, Grayslake, IL (US)

( * ) Notice: Subject to any disclaimer, the term of this patent is extended or adjusted under 35 U.S.C. 154(b) by 0 days.

(21) Appl. No.: 09/853,511

(22) Filed: May 11, 2001

Related U.S. Application Data

(63) Continuation-in-part of application No. 09/759,582, filed on Jan. 11, 2001, and a continuation-in-part of application No. PCT/US00/32000, filed on Nov. 21, 2000, and a continuation-in-part of application No. 09/651,455, filed on Aug. 30, 2000, and a continuation-in-part of application No. 09/651,763, filed on Aug. 30, 2000.
(60) Provisional application No. 60/266,617, filed on Feb. 6, 2001.

(51) Int. Cl.[7] ................................................ A61M 3/00
(52) U.S. Cl. ........................ 604/43; 604/6.16; 604/266
(58) Field of Search .......................... 604/43, 541, 264, 604/266, 270, 523, 528, 524, 4.01, 6.16

(56) References Cited

U.S. PATENT DOCUMENTS

| 1,879,249 A | 9/1932 | Honsaker |
| 2,116,083 A | 5/1938 | Rusch |
| 3,384,089 A | 5/1968 | Shriner |
| 3,589,368 A | 6/1971 | Jackson et al. |
| 4,037,599 A | 7/1977 | Raulerson |
| 4,134,402 A | 1/1979 | Mahurkar |
| 4,270,542 A | 6/1981 | Plumley |
| 4,311,140 A | 1/1982 | Bridgman |
| 4,368,737 A | 1/1983 | Ash |
| 4,381,011 A | 4/1983 | Somers, III |
| 4,445,897 A | 5/1984 | Ekbladh et al. |
| 4,498,902 A | 2/1985 | Ash et al. |
| 4,529,399 A | 7/1985 | Groshong et al. |
| 4,549,879 A | 10/1985 | Groshong et al. |
| 4,559,039 A | 12/1985 | Ash et al. |
| 4,568,329 A | 2/1986 | Mahurkar |
| 4,583,968 A | 4/1986 | Mahurkar |
| 4,623,327 A | 11/1986 | Mahurkar |
| 4,639,252 A | 1/1987 | Kelly et al. |
| 4,671,796 A | 6/1987 | Groshong et al. |

(List continued on next page.)

FOREIGN PATENT DOCUMENTS

GB  745379  2/1956

Primary Examiner—Brian L. Casler
Assistant Examiner—Jeremy Thissell
(74) Attorney, Agent, or Firm—Richard G. Lione; Brinks Hofer Gilson & Lione

(57) ABSTRACT

A hemodialysis catheter comprising a dual lumen tube with a bullet nose bolus at its distal end. A venous port is formed in one side of the bolus adjacent the bullet nose of the bolus. An arterial port is formed in the bolus circumferentially displaced 180° around the catheter from the venous port. The bolus contains a venous passage which transitions from a smaller diameter D-shaped cross-section to a larger diameter circular cross-section. The bullet nose is thinner than the tube but is inclined on an angle to the axis of the tube so that a portion of its outer periphery is substantially tangent to a hypothetical cylinder containing the trailing edge of the venous port.

48 Claims, 3 Drawing Sheets

U.S. PATENT DOCUMENTS

| | | |
|---|---|---|
| 4,692,141 A | 9/1987 | Mahurkar |
| 4,692,153 A | 9/1987 | Berlin et al. |
| 4,701,166 A | 10/1987 | Groshong et al. |
| 4,770,652 A | 9/1988 | Mahurkar et al. |
| 4,772,266 A | 9/1988 | Groshong |
| 4,781,678 A | 11/1988 | de Couët et al. |
| 4,808,155 A | 2/1989 | Mahurkar |
| 4,842,582 A | 6/1989 | Mahurkar |
| 4,895,561 A | 1/1990 | Mahurkar |
| 4,898,669 A | 2/1990 | Tesio |
| 5,053,004 A | 10/1991 | Markel et al. |
| 5,197,951 A | 3/1993 | Mahurkar |
| 5,221,255 A | 6/1993 | Maharkur et al. |
| 5,221,256 A | 6/1993 | Mahurkar |
| 5,322,519 A | 6/1994 | Ash |
| 5,336,177 A | 8/1994 | Marcus |
| 5,374,245 A | 12/1994 | Mahurkar |
| 5,378,230 A | 1/1995 | Mahurkar |
| 5,451,216 A | 9/1995 | Quinn |
| 5,486,159 A | 1/1996 | Mahurkar |
| 5,571,093 A | 11/1996 | Cruz et al. |
| 5,599,322 A | 2/1997 | Quinn |
| 5,607,405 A | 3/1997 | Decker et al. |
| 5,624,413 A | 4/1997 | Markel et al. |
| 5,685,836 A | 11/1997 | DiPerna et al. |
| 5,776,111 A | 7/1998 | Tesio |
| 5,947,953 A | 9/1999 | Ash et al. |
| 5,984,913 A | 11/1999 | Kritzinger et al. |

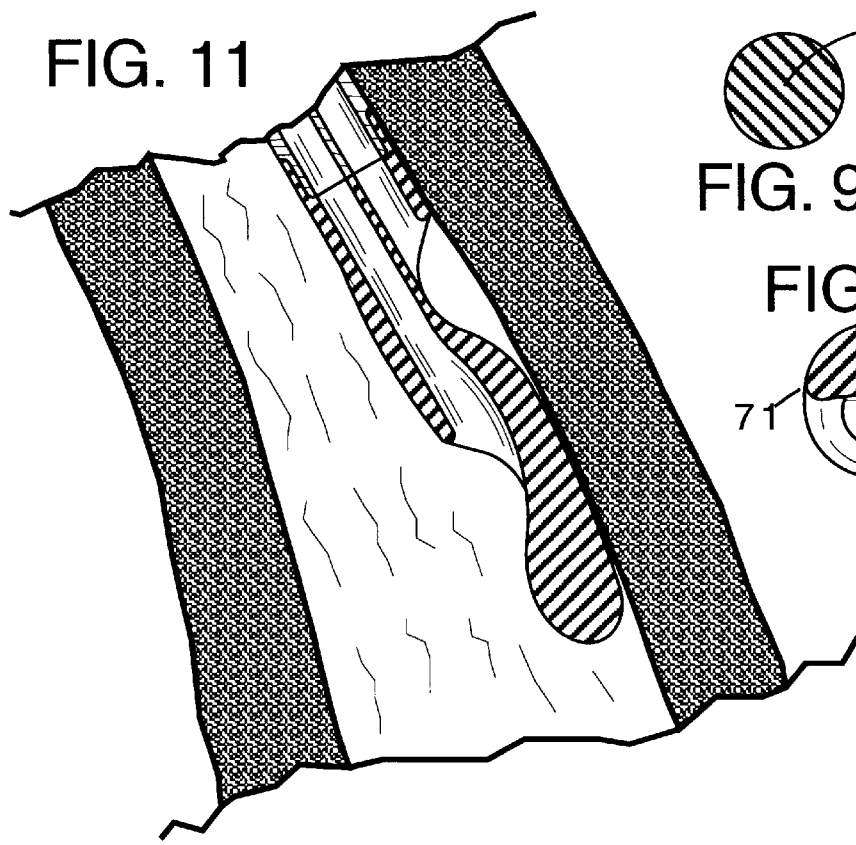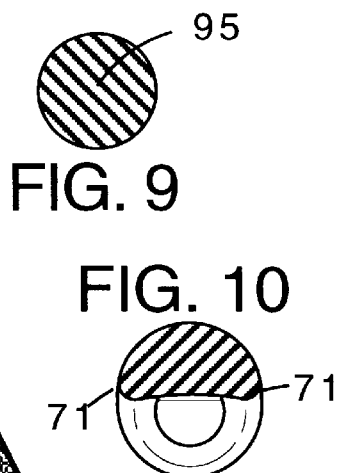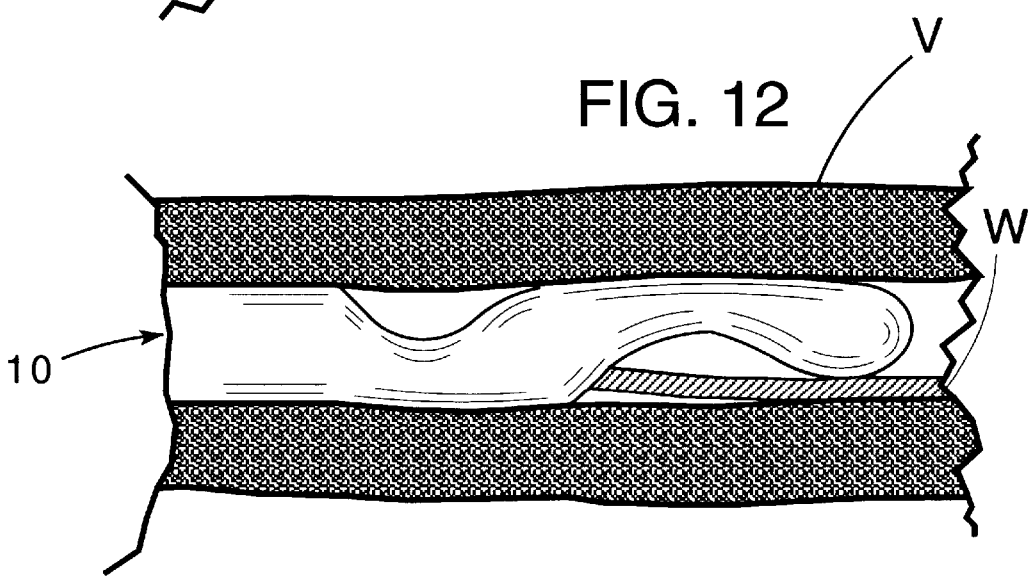

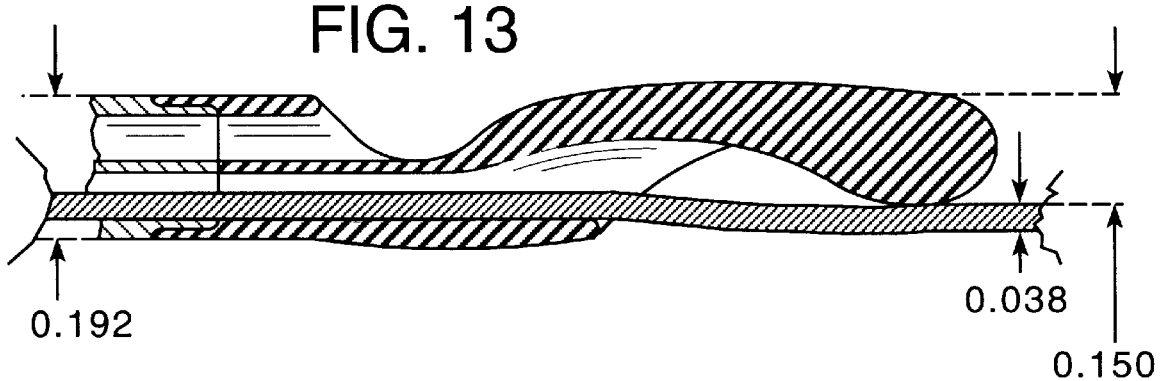
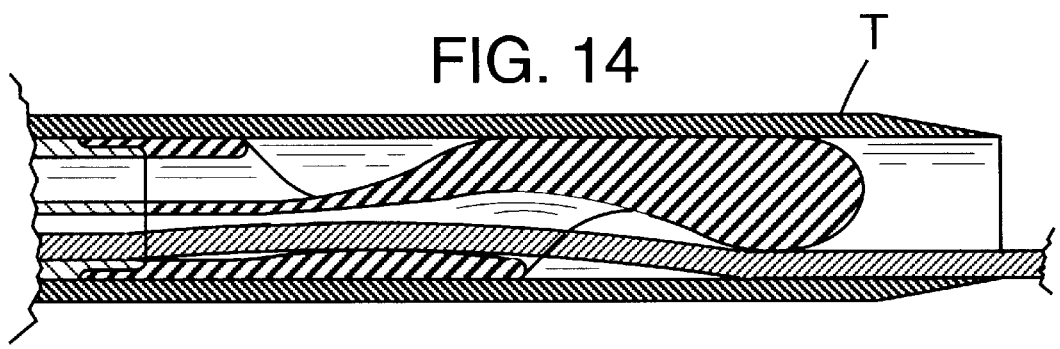
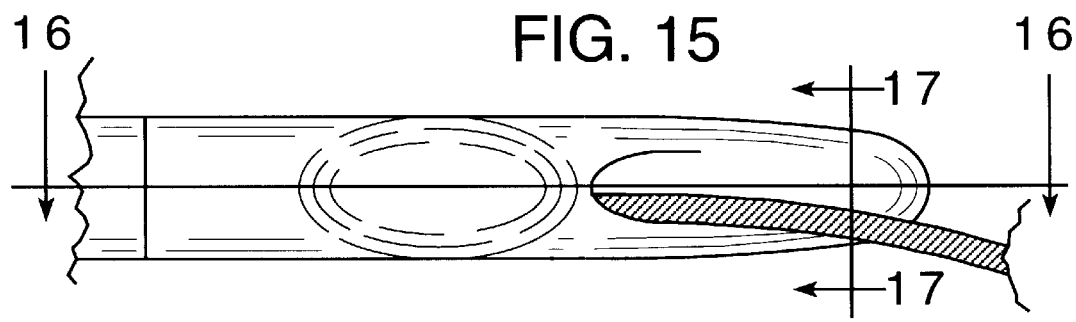
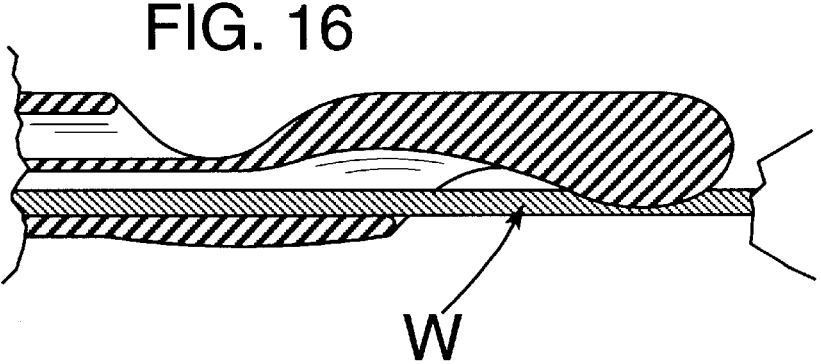
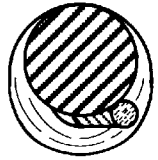

HEMODIALYSIS CATHETER

RELATED APPLICATIONS

This application is a continuation-in-part of U.S. application Ser. No. 09/651,455 filed Aug. 30, 2000, U.S. application Ser. No. 09/651,763 filed Aug. 30, 2000, PCT application Ser. No. PCT/US00/32000 filed Nov. 21, 2000, U.S. application Ser. No.09/759,582, filed Jan. 11, 2001, and provisional U.S. application Ser. No. 60/266,617, filed Feb. 6, 2001.

FIELD OF THE INVENTION

This invention relates in general to hemodialysis. It relates, more particularly, to hemodialysis catheters.

BACKGROUND OF THE INVENTION

Hemodialysis, as practiced today, normally employs one of two types of catheter to remove blood from the patient for processing and return processed blood to the patient. Most commonly, a catheter tube containing two lumens is used, each lumen having a generally semi-cylindrical or D-shape configuration. This type of catheter is frequently referred to as a dual lumen catheter. Alternatively, two tubes, each with a full cylindrical configuration, are used separately to remove blood for dialysis and return the processed blood.

Flow rates possible with conventional dual lumen catheters are usually lower than those achievable where separate tubes are used to remove blood from a vein for dialysis and then return processed blood back to the vein.

Thus, the use of two tubes has become more and more popular as the capacity (maximum flow rate) of hemodialysis membranes has increased.

Hemodialysis membranes are now able to process blood at over 500 ml of flow per minute. Even higher processing rates are foreseeable. However, problems occur with both the line introducing purified blood back into the vein (the venous or outflow line) and the line removing blood for purification (the arterial or intake line) at flow rates above 300 ml per minute. A high flow rate from the venous line may cause whipping or "firehosing" of the tip in the vein with consequent damage to the vein lining. A corresponding high flow rate into the arterial line may cause the port to be sucked into the vein wall, resulting in occlusion. It should be understood, of course, that both lines normally access the superior vena cava and the designations are used for differentiation purposes.

Speed of flow through a catheter lumen, whether it be in a single lumen or a dual lumen catheter, is controlled by a number of factors including the smoothness of the wall surface, the internal diameter or cross-sectional area of the tube lumen, and the length of the tube lumen. The most important factor is the cross-sectional area of the tube lumen. The force or speed of the fluid flow in a tube lumen for a given cross-sectional area is controlled by the external pumping force, of course. This is a positive pressure pushing processed blood through the venous lumen and a negative (suction) pressure pulling unprocessed blood through the arterial lumen.

Problems encountered in providing for a high flow rate through a catheter are magnified in a dual lumen catheter construction. Because each of the lumens in a dual lumen catheter normally has a D-shape, it has been assumed that flow rates are limited. Furthermore, such dual lumen catheters are, to a great extent, catheters with a main port which opens at the end of a lumen substantially on the axis of the lumen. Thus, "firehosing" frequently results. Fire-hosing may damage the vein wall, triggering the build-up of fibrin on the catheter tip. Fibrin build-up may result in port occlusion.

There are dual lumen catheters which utilize side ports for both outflow and inflow. An example is the catheter disclosed in the Cruz et al. U.S. Pat. No. 5,571,093. However, such catheters have not been entirely successful in solving problems related to hemodialysis with dual lumen catheters, e.g., high incidences of catheter port occlusion as well as some degree of fire-hosing.

Catheters of almost all types are also pliable so that they do not damage body tissue when they are in-situ. Pliability can create a problem during insertion, however, because the catheters can kink when they meet resistance. Thus, there is often a need for a certain amount of stiffness so that the catheters can be directed within body vessels or cavities. There are currently two methods of providing this stiffness; stylets and guide wires.

A stylet can be a single or a twisted wire with a blunt end that is inserted into the catheter to make it stiff. The stylet is often used with bullet nose catheters and maintains its position within the catheter as the catheter is inserted. The stiffened catheter is advanced into the blood vessel with the stylet.

In contrast, guide wires are used to both stiffen the catheter and to provide a guide for the insertion. Commonly, the guide wire is inserted into the blood vessel before the catheter. The catheter is then inserted into the blood vessel over the wire, and follows the wire as it travels inside the vessel. Guide wires are most often utilized with catheters that are inserted deep into the body, such as with central venous catheters that are inserted into the heart. The thin guide wire more easily makes the bends and turns necessary for this type of placement.

In guide wire insertion where the catheter must be inserted over the guide wire, catheters with open ends are normally utilized to permit passage of the guide wire. These catheters are more likely to cause damage to body tissue during insertion than bullet nose catheters, for example, because of their flat ends and side edges. Open ended catheters are also more likely to damage tissue than bullet nose catheters while in-situ. Nevertheless, the need for deep catheter insertion has heretofore made guide wire insertion of open-ended catheters the accepted procedure in spite of the disadvantage of their flat or blunt end design.

As an alternative, bullet nose catheters have occasionally been used with guide wires in some applications by incorporating a small hole through the nose for the wire to pass through. This approach has generally been found undesirable, however, because the hole in the bullet nose can later collect particulate matter and be a focal point for infection.

SUMMARY OF THE INVENTION

An object of the invention is to provide an improved dual lumen hemodialysis catheter.

Another object is to provide a dual lumen hemodialysis catheter which accommodates flow rates substantially as high as the latest separate lumen catheters.

Still another object is to provide a dual lumen hemodialysis catheter which is capable of returning processed blood to the patient at high flow rates without harmful firehosing of the catheter tip.

Yet another object is to provide a dual lumen hemodialysis catheter which permits high flow rates while minimizing trauma and potential red cell damage so as to substantially avoid clotting.

A further object is to provide a dual lumen hemodialysis catheter which substantially reduces the incidence of port occlusion.

Still a further object is to provide a dual lumen hemodialysis catheter in which occlusion of the return line port is substantially avoided regardless of the flow rate.

Still a further object is to provide a dual lumen hemodialysis catheter which facilitates reversal of the venous and arterial lines to relieve port occlusion without increasing the potential for mixing of dialyzed blood with blood being removed for dialysis Another object of the invention is to provide an improved bullet nose bolus for use on catheters ranging in size from 3 French to 22 French in any medical application.

A further object is to provide a bullet nose bolus that protects the leading edge of the catheter outflow or inflow port from rubbing against the vessel wall.

Another object is to provide a bullet nose bolus for a catheter that will not kink during insertion.

Another object of the present invention is to provide an improved catheter for use with a guidewire.

Still another object is to provide a bullet nose bolus for a catheter which is compatible with a guide wire yet does not require an axially extending hole through the nose.

Another object is to provide a bullet nose bolus for a catheter that can be inserted simultaneously with a guide wire through a flexible introducer sheath that is essentially the same size as the catheter itself.

Another object is to provide a bullet nose bolus for a catheter that follows a guide wire through bends in a patient's vein and turns without causing increased resistance to passage through the vein.

Another object is to provide a bullet nose bolus that always presents a rounded surface to the vein wall, even when the catheter is following a guide wire around a bend.

Another object is to provide a bolus with a nose which is designed to flex away from the guide wire in only one direction.

The foregoing and other objects are realized in accord with the present invention by providing a dual lumen hemodialysis catheter including a bullet-nose bolus having a radially opening outflow or venous port and a radially opening intake or arterial port The arterial port is circumferentially displaced 180° around the bolus from the venous port.

The venous port opens radially through the bolus immediately behind its bullet nose. The D-shape venous lumen in the catheter tube communicates with a corresponding D-shape venous passage in the body of the bolus. That D-shape venous passage transitions into a circular cross-section venous passage before reaching the venous port, while increasing in cross-sectional area from the D-shape passage to the circular passage.

The arterial port is axially displaced from the venous port and opens radially through the bolus immediately behind the venous port, albeit 180° displaced therefrom. The arterial port communicates directly with a corresponding D-shape arterial passage in the body of the bolus.

In front of the arterial port and opposite the venous port, the profile of the bolus curves in an arc toward the side of the bolus in which the venous port is disposed, creating a stiffening arch in the passage section opposite the venous port. From the trailing edge of the venous port forward, the passage section and the nose section are effectively inclined to the longitudinal axis of the bolus and tube, and toward the venous port side of the bolus. The bullet nose of the nose section is thus offset from the axis of the bolus toward the venous port.

The opposite side surfaces of the bolus, proceeding forward from the mid-point of the venous port, also taper inwardly in converging arcs to the bullet nose section. Thus, the bolus nose section is both narrower in width and thinner in height than the trailing remainder of the bolus and the catheter tube itself.

Where the passage section joins the nose section of the bolus, on a plane extending transversely through the bolus in front of the venous port, the nose section has a maximum thickness in the plane on a line passing through the bolus axis and the center of the venous port. The thickness of the nose section is 20% to 25% less than the diameter of the catheter tube itself. The plane is inclined forwardly away from the port at an angle corresponding to the angle of inclination of the curving passage section toward the bolus axis.

The nose section of the bolus, being not as thick as the rest of the bolus but displaced radially to the venous port side of the longitudinal axis of the bolus passage section and catheter tube, is in a position wherein a portion of its outermost periphery is tangent to an imaginary cylinder containing the outer surface of the bolus passage section at the trailing edge of the venous port. This offset nose configuration prevents the vein wall from wrapping around the trailing edge of the port and being abraded thereby.

The stiffening arch defined in the bolus opposite the venous port inhibits folding of the bolus at the venous port during insertion of the catheter. Immediately opposite the arterial port, another stiffening arch is also formed in the bolus. The arch extends along that side of the bolus from a point radially aligned with the trailing edge of the arterial port to the trailing edge of the venous port. This arch inhibits folding of the bolus around the arterial port.

The catheter of the invention, with its novel bolus, lends itself ideally to insertion in a patient's vein over a guide wire. When inserted through the vein the bullet nose section flexes radially outwardly in a plane passing through the bolus axis and both ports under the influence of the guide wire. Because the nose section has a smaller thickness in that plane than the rest of the bolus and the tube, however, it is not forced outside the imaginary cylinder of the catheter. This makes for ease of insertion.

BRIEF DESCRIPTION OF THE DRAWINGS

The invention, including its construction and method of operation, is illustrated more or less diagrammatically in the drawings in which:

FIG. 6 is a cross-sectional view taken along line 6—6 of FIG. 1;

FIG. 7 is a cross-sectional view taken along line 7—7 of FIG. 1;

FIG. 8 is a cross-sectional view taken along line 8—8 of FIG. 1;

FIG. 9 is a cross-sectional view taken along line 9—9 of FIG. 1;

FIG. 10 is a cross-sectional view taken along line 10—10 of FIG. 1;

FIG. 11 is a longitudinal sectional view through a patient's vein with a catheter in-situ in a typical operational position;

FIG. 12 is a longitudinal sectional view similar to FIG. 5 showing the bolus nose section flexed upwardly by a guide wire;

FIG. 13 is a longitudinal sectional view of a catheter being inserted over a guide wire through a patient's vein;

FIG. 14 is a longitudinal sectional view of a catheter prepared for introduction into a patient's vein over a guide wire and through an introducer tube;

FIG. 15 is a bottom plan view of a catheter bolus and guide wire showing their relative orientation as the catheter is led around a turn in a patient's vein;

FIG. 16 is a longitudinal sectional view taken along line 16—16 of FIG. 15; and

FIG. 17 is a cross-sectional view taken along line 17—17 of FIG. 15.

DESCRIPTION OF THE PREFERRED EMBODIMENT

Figure 1:
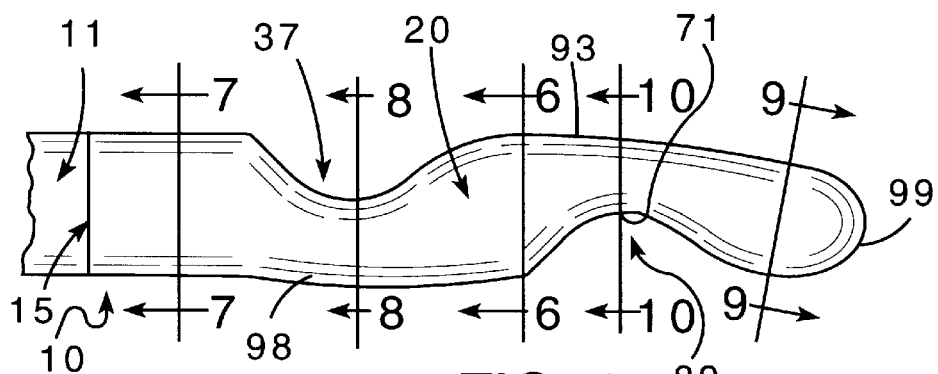
FIG. 1 is a side elevational view of a portion of a hemodialysis catheter embodying features of the invention.
Figure 2:
FIG. 2 is a front end view of the catheter bolus.
Figure 3:
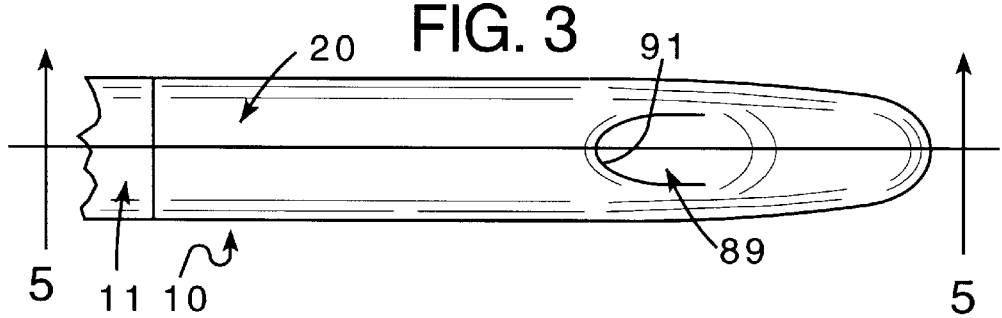
FIG. 3 is a bottom plan view of the bolus end of the catheter of FIG. 1.
Figure 4:
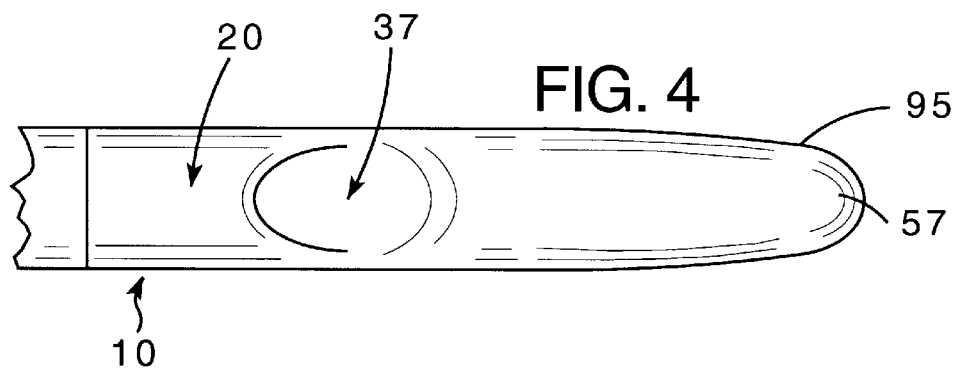
FIG. 4 is a top plan view of the bolus for the catheter of FIG. 1.

Referring now to the drawings and particularly to FIGS. 1–4, a dual lumen catheter embodying features of the invention is illustrated generally at 10. The catheter 10 comprises a cylindrical tube 11 (only partially shown) having a distal end 15. A bolus 20 is attached to the distal end 15 of the tube 11.

Figure 5:
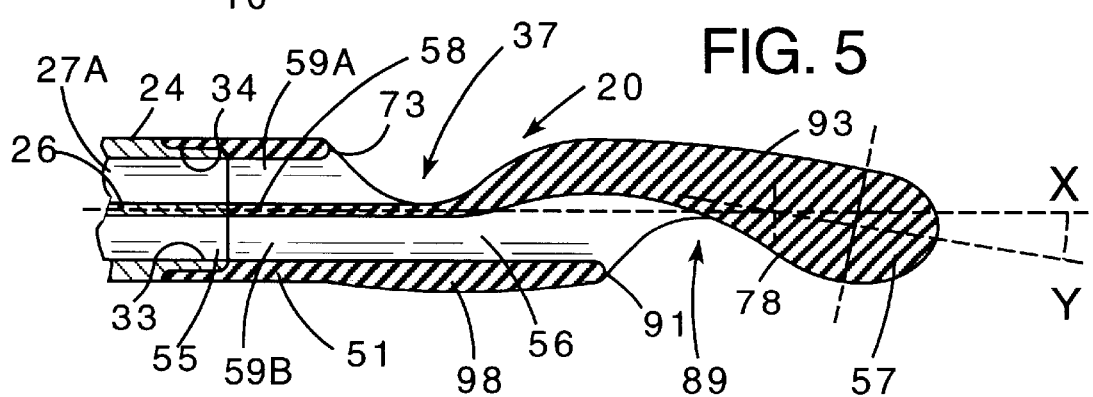
FIG. 5 is a longitudinal sectional view taken through the bolus of the catheter of FIG. 4.

Referring now also to FIGS. 5–10, the tube 11 illustrated is a 14.5 French tube formed of a plastic material such silicone or polyurethane. In its preferred form, the tube is formed of MED-4700-A&B silicone manufactured by NuSil Technologies. The tube 11 is formed by extruding a tubular body 24 with a generally cylindrical wall 25 and a septum 26. The 14.5 French tube 11 has an O.D. of 0.192 inches.

The tube body 24 is divided by the septum 26 into two identical D-shape lumens 27A and 27B extending through the tube body along its length. The lumen 27A is normally an arterial lumen and the lumen 27B is normally a venous lumen. Each lumen 27A and 27B has a D-shape cross-sectional area of about 0.006 $in^2$ in a 14.5 French dual lumen tube.

The distal end 15 of the dual lumen tube body 24 has a necked down end 33 which is seated in a suitably formed socket 34 in the bolus 20. The bolus 20 has a body 51 also formed of silicone or polyurethane. The tube 11 and bolus 20 are mated in this relationship after each is formed. When silicone is used, for example, and the combination is cured, mated portions of the tube 11 and the bolus 20 are effectively welded together.

The bolus body 51 includes a tube connector section 55, a flow passage section 56 and a nose section 57. The flow passage section 55 has a septum 58 formed in it. The septum 58 mates, end-to-end, with the septum 26 in the tube body 24, and they are welded together.

The septum 58 forms upper and lower passages 59A and 59B in the flow passage section 56. The upper passage 59A is normally an arterial passage. The lower passage 59B is normally a venous passage.

The upper arterial passage 59A has a D-shape cross-section and extends forwardly with, and above, the septum 58 to the radial arterial port 37. Like the lumen 27A, the passage 59A has a cross-sectional area of about 0.006 $in^2$. The radial arterial port 37 extends circumferentially around the body's axis from the upper surface of the septum 58 on one side of the tube to the upper surface of the septum on its other side. The leading edge 73 of the bolus body 51 above the passage 59A, which forms the trailing edge of the port 37, is rounded along its length down to the septum 58 (see FIG. 4).

Forward of the arterial port 37 the bolus body 51 becomes solid, as at 76. In effect, the arterial passage 59A disappears and the septum 58 melds into this solid portion 76 of the bolus body 51.

Meanwhile, the venous passage 59B has a D-shape cross-section portion with a cross-sectional area of about 0.006 $in^2$ extending forwardly until the septum 58 ends. The venous passage 59B then gradually increases in size as it changes from a D-shape to a circular cross-section, as seen in FIG. 6. The circular cross-section of the passage 59B at the section line 6—6 has a cross-sectional area of about 0.007 $in^2$.

The cross-section of the passage 59B becomes fully circular (at section line 6—6) where it emerges over a base 78 which curves across the body 51 to form the front end of an axially elongated main outflow or venous port 89 in the body. The port 89 extends circumferentially around the body 51 to its side edges 71, as seen in FIG. 10. There it will be seen that the port 89 extends around approximately 230° of the circular cross-section passage 59B where it opens over the base 78 of the port. The port 89 has a trailing edge 91. The edge 91 is semi-circular in cross-section rounded along its length (see FIG. 5).

Where the port 89 begins, at its trailing edge 91, the outer surface of the solid portion 76 in the bolus body 51 opposite the port begins to curve inwardly to form a stiffening arch 93. The curve continues to where the arch 93 joins the nose section 57 at the base 95 of this section and then forwardly to the rounded bullet nose 99 on the nose section. The effective longitudinal axis Y of the passage section 57 forward of the trailing edge 91 of the port 89 is inclined to the longitudinal axis X of the trailing portion of the bolus body 51 at an angle of 9°. The arch 93 stiffens the bolus body 51 opposite the port 89 to prevent folding or kinking of the bolus 20 at that point as it travels through a vein during insertion.

Meanwhile, opposite the port 37 and behind the port 89, the bolus body is curved outwardly and then inwardly to form a stiffening arch 98. The arch 98 stiffens the bolus body 51 in the region of the port 37. The arch 98 serves to prevent folding or kinking of the bolus body 51 during insertion.

The side surfaces 101 and 102 of the bolus body 51, forward of the mid-point in the axially elongated port 89 and bracketing the arch 93, also curve inwardly to the nose section 57. This shape inhibits lateral flexing of the bolus nose section 57 during insertion.

The nose section 57 has a slightly elliptical shape in cross-section on the inclined plane P where it meets the nose section (see FIG. 9). The plane P is inclined forwardly relative to the axis X at an angle of about 81°. On the plane P, the nose section 57 is smaller in both width and thickness than the 14.5 French tube 11. In its preferred form, it is only about 10 French in size at this point and has a thickness of 0.150 inches which is 22% less than the diameter of the tube 11. In addition, the center of the nose section 57 on the axis Y is offset from the center of the bolus body 51 in the direction of the port 89.

The aforedescribed size, shape and orientation of the nose section 57 in the bolus body 51 provides several important advantages in use of the catheter 10. First, its smaller size facilitates easy entry into, and travel through, a patient's vein by the bolus 20. Second, the offset nose section 57 places a portion of its periphery tangent to a hypothetical cylinder in which the outer surface of the bolus passage section 56 lies, even though it is considerably thinner than the remainder of the bolus. This prevents the vein wall from wrapping inwardly about the edge 91 of the port 89 and the edge then abrading the vein wall. Third, when guide wire insertion is employed, the nose section 57 flexes radially away from the wire where it emerges from the port 89, without forcing either the nose section or the wire substantially outside the aforementioned cylinder into the vein wall. Fourth, when traveling around curves in a vein during insertion, the bolus nose resists bending sideways and catching on the vein wall.

In regard to the second advantage referred to, attention is invited to FIG. 11 which shows the catheter 10 in a typical position in a vein V. There it will be seen that the periphery of the nose section 57 engages a vein wall when the passage section 56 does. This prevents the trailing edge 91 of the port 89 from having the vein wall wrap on it and become abraded.

During insertion, as seen in FIG. 12, the guide wire W causes the nose section 57 to flex outwardly until its axis Y is substantially parallel to the axis X of the bolus. However, the nose section 57, having a smaller cross-section generally and a smaller thickness particularly, does not protrude measurably outside the aforementioned cylinder. FIG. 13 shows the relative dimensions of the bolus 20 of the invention on a 10.5 French tube as it is inserted over a wire W, the inclined nose section 57 being flexed radially by the wire W but not outside the aforedescribed hypothetical cylinder. There it will be seen that the diameter of the tube 11 is 0.192 inches while the combined thickness of the wire W and nose section 57 is 0.188 inches.

As seen in FIG. 14, when the catheter 10 is inserted into an introducer tube T, the hose section 57 of the bolus 20 flexes upwardly to let the wire W pass. Because the nose section 57 has a smaller cross-section than the rest of the bolus body 51 and the tube 11, it is not compressed against the vein wall and frictional resistance to its passage is not measurably increased.

FIGS. 15–17 illustrate the catheter bolus 20 following the guide wire W around a turn in a vein (not shown). Here it will be seen that the wire W moves to one side of the nose section 57 and nestles alongside it. The bolus 57 sides curve inwardly from the mid-point of the port 89 forward, as has previously been pointed out. This shape tends to stiffen the bolus tip against lateral flexing.

With the catheter 10 in use in a patient, it has a number of important operational characteristics, some of which will be emphasized here. Because the lumen 59B in the bolus body 51 increases in size and becomes circular in cross-section as it approaches the port 89, pressure decreases, flow is more uniform and dialyzed blood is discharged through the venous port under less force. Should the arterial port 37 become clogged, the flow can be reversed to introduce dialyzed blood through port 37 and clear the port 37. Since the port 89 is relatively far removed from the port 37, dialyzed blood is not sucked directly into the port 89.

The present invention provides the physician with a bullet nose catheter 10 which can be inserted using a guide wire W but which does not require perforation of the bolus nose to facilitate passage of the guide wire. The nose section 57 of the bolus 20 flexes away from the bolus axis X to permit passage of the wire W but, in doing so, does not protrude measurably outside the imaginary cylinder defined by the rest of the bolus and the catheter tube, whereby the pressure of the bolus on vein V wall is not increased. Nevertheless, with the catheter 10 in operational position in a patient's vein V and the wire W removed, the nose section returns 57 to its normal position wherein it prevents the vein wall from wrapping around the bolus port edge 91 and becoming abraded thereby.

While a preferred embodiment of the invention has been described, it should be understood that the invention is not so limited and modifications may be made without departing from the invention. The scope of the invention is defined by the appended claims, and all devices that come within the meaning of the claims, either literally or by equivalence, are intended to be embraced therein.

What is claimed is:

1. A bolus for a hemodialysis catheter, comprising:
   a) a general cylindrical body molded of resilient plastic and including a rear connector section, a front nose section and an intermediate passage section;
   b) said passage section containing first and second axially extending passages having a septum therebetween, said first passage communicating with a first port opening radially out of said cylindrical body in said passage section, said second passage communicated with a second port opening radially out of said cylindrical body in said passage section;
   c) said nose section having a bullet nose and joining said passage section immediately at the front end of said second port and;
   d) the thickness of said nose section where it joins said passage section at the front end of said second port being substantially less than the diameter of said passage section behind said second port.

2. The bolus of claim 1 further characterized in that:
   a) said bolus body includes an axially extending stiffening arch formed in its outer periphery opposite said second port.

3. The bolus of claim 1 further characterized in that:
   a) said bolus body includes an axially extending stiffening arch formed in its outer periphery opposite said first port.

4. The bolus of claim 1 further characterized in that:
   a) said first passage has a substantially uniform cross-sectional area along substantially its entire length; and
   b) said second passage has one cross-sectional area adjacent said connector section and another cross-sectional area where it communicates with said second port, said other cross-sectional area being greater than said one cross-sectional area.

5. The bolus of claim 1 further characterized in that:
   a) said nose section is offset to one side of the longitudinal axis of said bolus in the direction of said second port so that a portion of the outer periphery of said bullet nose section normally is substantially tangent to an imaginary cylinder containing the outer surface of said passage section immediately behind said second port.

6. The bolus of claim 1 further characterized in that:
   a) said nose section is approximately elliptical in cross-section where it joins said passage section.

7. The bolus of claim 1 further characterized in that:
   a) said bolus has side surfaces which, approximately at the mid-point of said second port, begin converging toward the axis of said bolus.

8. The bolus of claim 1 further characterized in that:
   a) said second passage has a substantially circular cross-section where it communicates with said second port; and b) said second port extends circumferentially around more than 180° of the circumference of said second passage.

9. The bolus of claim 1 further characterized in that:
a) said second port has a trailing edge, the portion of said passage section in front of said trailing edge being inclined to the longitudinal axis of said bolus.

10. A bolus for a hemodialysis catheter, comprising:
a) a general cylindrical body molded of resilient plastic and including a rear connector section, a front nose section and an intermediate passage section arranged in axially aligned relationship;
b) said intermediate passage section containing first and second axially extending passages having a septum therebetween, said first passage communicating with a first port opening radially out of said cylindrical body in said passage section, said second passage communicated with a second port opening radially out of said cylindrical body in said passage section;
c) each of said ports having a trailing edge extending around a portion of the circumference of said bolus body;
d) said front nose section having a rounded bullet nose;
e) said second passage having one cross-sectional area adjacent said connector section and another cross-sectional area where it communicates with said second port, said other cross-sectional area being greater than said one cross-sectional area.

11. The bolus of claim 10 further characterized in that:
a) said bolus body includes an axially extending stiffening arch formed in its outer periphery opposite said second port.

12. The bolus of claim 10 further characterized in that:
a) said bolus body includes an axially extending stiffening arch formed in its outer periphery opposite said first port.

13. The bolus of claim 10 further characterized in that:
a) said front nose section begins at the front end of said second port and has a maximum thickness at that point which is less than the outside diameter of said passage section at said trailing edge of said second port.

14. The bolus of claim 13 further characterized in that:
a) said bolus body includes an axially extending stiffening arch formed in its outer periphery opposite said second port.

15. The bolus of claim 13 further characterized in that:
a) said bolus body includes an axially extending stiffening arch formed in its outer periphery opposite said first port.

16. The bolus of claim 10 further characterized in that:
a) said nose section has a center which is offset to one side of the longitudinal axis of said bolus in the direction of said second port so that a portion of the outer periphery of said bullet nose section normally is substantially tangent to an imaginary cylinder containing the outer surface of said passage section.

17. The bolus of claim 10 further characterized in that:
a) said nose section is elliptical in cross-sectional configuration where it joins said passage section.

18. The bolus of claim 10 further characterized in that:
a) said bolus body has converging side walls from about the mid-point of said second port forwardly.

19. The bolus of claim 10 further characterized in that:
a) first port extends around less than 180° of the circumference of said bolus body; and
b) said second port extends around more than 180° of the circumference of said second passage where it communicates with said second port.

20. The bolus of claim 10 further characterized in that:
a) each of said trailing edges is approximately semi-circular in cross-section along its entire length.

21. A bolus for a hemodialysis catheter, comprising:
a) a general cylindrical body molded of resilient plastic and including a rear connector section, a front nose section and an intermediate passage section arranged in axially aligned relationship;
b) said intermediate passage section containing first and second axially extending passages having a septum therebetween, said first passage communicating with a first port opening radially out of said cylindrical body in said passage section, said second passage communicated with a second port opening radially out of said cylindrical body in said passage section;
c) each of said ports having a trailing edge extending around a portion of the circumference of said bolus body;
d) said front nose section having a maximum thickness which is less than the diameter of the trailing portion of the bolus and having a rounded bullet nose;
e) said front nose section also having a longitudinal axis which is inclined to the longitudinal axis of said bolus in the direction of said second port so that a portion of the outer periphery of said bullet nose section is normally substantially tangent to an imaginary cylinder containing the outer surface of said passage section at said trailing edge of said second port even though its maximum thickness is less than the diameter of the trailing portion of the bolus.

22. The bolus of claim 21 further characterized in that:
a) said front nose section beginning at the front end of said second port and having a cross-section at that point which are less than the cross-sectional of said passage section.

23. The bolus of claim 21 further characterized in that:
a) said bolus body includes an axially extending stiffening arch formed in its outer periphery opposite said second port.

24. The bolus of claim 21 further characterized in that:
a) said bolus body includes an axially extending stiffening arch formed in its outer periphery opposite said first port.

25. The bolus of claim 21 further characterized in that:
a) said first passage has a substantially uniform cross-sectional area along substantially its entire length; and
b) said second passage has one cross-sectional area adjacent said connector section and another cross-sectional area where it communicates with said second port, said other cross-sectional area being greater than said one cross-sectional area.

26. The bolus of claim 21 further characterized in that:
a) said bullet nose section is elliptical in cross-sectional configuration where it joins said passage section.

27. The bolus of claim 21 further characterized in that:
a) said bolus body narrows in plan configuration from the mid-point of said second port forwardly.

28. The bolus of claim 21 further characterized in that:
a) said first port extends around less than 180° of the circumference of said bolus body; and
b) said second port extends around more than 200° of the circumference of said second passage.

29. The bolus of claim 21 further characterized in that:
a) each of said trailing edges is approximately semi-circular in cross-section along its entire length.

30. A hemodialysis catheter including a dual lumen tube and a bolus on a distal end of said tube, said bolus comprising:
   a) a bolus body molded of plastic in a generally cylindrical shape about a longitudinal axis, said bolus body having first and second axially extending passages therein, said first passage terminating in a radially extending first port and said second passage terminating in a radially extending second port;
   b) said radially extending first and second ports being angularly displaced from each other around the axis of said bolus body;
   c) said bolus body including a nose section forming a rounded front end on said bolus, the center of said nose section being radially offset from the axis of the bolus itself in the angular direction of said second port.

31. The bolus of claim 30 further characterized in that:
   a) said second passage includes a passage portion having a D-shape cross-section and a passage portion having a cross-section of another shape;
   b) said passage portion with a cross-section of said other shape having a larger cross-section than said D-shape cross-section portion.

32. The bolus of claim 31 further characterized in that:
   a) said cross section of said other shape being circular.

33. The bolus of claim 31 further characterized in that:
   a) said bolus body has an axially elongated stiffening arch formed in its outer surface opposite said second port.

34. The bolus of claim 33 further characterized in that:
   a) said bolus body has an axially elongated stiffening arch formed in its outer surface opposite said first port.

35. The bolus of claim 33 further characterized in that:
   a) said stiffening arch extends radially inwardly from an outermost end adjacent said first port to an innermost end adjacent said nose section.

36. The bolus of claim 30 further characterized in that:
   a) said first and second ports being angularly displaced from each other by about 180°.

37. A hemodialysis catheter including a dual fumen tube and a bolus on a distal end of said tube, said catheter comprising:
   a) a tube body containing first and second lumens; and
   b) a bolus body molded of resilient plastic in a generally cylindrical shape about a longitudinal axis;
   c) said bolus body having first and second axially extending passages therein; said first passage terminating in a radially extending first port in the side of said body and said second passage terminating in a radially extending second port in the side of said body;
   d) said radially extending first and second ports being angularly displaced from each other approximately 180° around the axis of said bolus body;
   e) said first port extending circumferentially around said bolus body for less than 180°;
   f) said second port extending circumferentially around said bolus body for less than 180° but extending circumferentially around said second passage section where it communicates with said second port for more than 200°;
   g) said bolus body including a nose section forming a rounded front end on said bolus in front of said second port.

38. The catheter of claim 37 further characterized in that:
   a) said nose section is, at its largest cross-section, substantially smaller in cross-section than the rest of said bolus body.

39. The catheter of claim 38 further characterized in that:
   a) the longitudinally axis of said nose section is inclined to the longitudinal axis of the bolus itself whereby said nose section is directly in front of said second port.

40. The catheter of claim 39 further characterized in that:
   a) said bolus body includes an axially extending stiffening arch formed in its outer periphery opposite said second port.

41. The catheter of claim 39 further characterized in that:
   a) said bolus body includes an axially extending stiffening arch formed in its outer periphery opposite said first port.

42. The catheter of claim 39 further characterized in that:
   a) said first passage has a substantially uniform cross-sectional area along substantially its entire length; and
   b) said second passage has one cross-sectional area adjacent said connector section and another cross-sectional area where it communicates with said second port, said other cross-sectional area being greater than said one cross-sectional area.

43. The catheter of claim 39 further characterized in that:
   a) said second passage includes a passage portion having a D-shape cross-section and a passage portion having a cross-section of another shape;
   b) said passage portion with a cross-section of said other shape having a larger cross-section than said D-shape cross-section portion.

44. The bolus of claim 33 further characterized in that:
   a) said cross-section of said other shape is circular.

45. The bolus of claim 34 further characterized in that:
   a) said bolus body has an axially elongated stiffening arch formed in its outer surface opposite said second port.

46. The bolus of claim 35 further characterized in that:
   a) said bolus body has an axially elongated stiffening arch formed in its outer surface opposite said first port.

47. The bolus of claim 36 further characterized in that:
   a) said stiffening arch curves radially inwardly relative to the longitudinal axis of the bolus from an outermost end adjacent said first port to an innermost end adjacent said nose section.

48. A hemodialysis catheter comprising:
   a) a tube containing a first substantially D-shape lumen and a second substantially D-shape lumen, said tube having a distal end through which said lumens open;
   b) an axially elongated bolus having a connector section connected to said distal end of said tube, a passage section containing a first axially extending passage and a second axially extending passage and a nose section;
   c) said nose section having a rounded nose which is unperforated axially of the bolus;
   d) said passage section also containing a first radially extending port communicating with said first passage and a second radially extending port communicating with said second passage;
   e) said nose section beginning immediately adjacent the front end of said second port;
   f) said nose section having a maximum thickness which is at least 20% less than the outside diameter of said tube;
   g) said second passage including a D-shape cross-section portion adjacent said connector section and a substantially circular cross-section portion adjacent said second port;
   h) said radially extending ports being disposed on different radials from the longitudinal axis of said bolus.

* * * * *